(12) United States Patent
Song (10) Patent No.: US 8,970,831 B2
(45) Date of Patent: Mar. 3, 2015

(54) OPTICAL CONSTANT MEASURING APPARATUS AND METHOD THEREOF

(71) Applicant: Electronics and Telecommunications Research Institute, Daejeon (KR)

(72) Inventor: Hyun Woo Song, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 240 days.

(21) Appl. No.: 13/678,453

(22) Filed: Nov. 15, 2012

(65) Prior Publication Data

US 2013/0135611 A1    May 30, 2013

(30) Foreign Application Priority Data

Nov. 29, 2011   (KR) .................. 10-2011-0126264

(51) Int. Cl.
| | |
|---|---|
| *G01N 21/00* | (2006.01) |
| *G01N 21/55* | (2014.01) |
| *G01N 21/21* | (2006.01) |
| *G01N 21/47* | (2006.01) |

(52) U.S. Cl.
CPC .............. *G01N 21/55* (2013.01); *G01N 21/21* (2013.01); *G01N 21/4795* (2013.01)
USPC ....................................................... 356/73

(58) Field of Classification Search
USPC ...................................................... 356/72–73
See application file for complete search history.

(56) References Cited

U.S. PATENT DOCUMENTS

| 5,936,726 A * | 8/1999 | Takeda et al. ............. 356/237.2 |
| 6,684,099 B2 | 1/2004 | Ridder et al. |
| 7,315,767 B2 | 1/2008 | Caduff et al. |

OTHER PUBLICATIONS

Gerald L. Coté et al., "Noninvasive optical polarimetric glucose sensing using a true phase measurement technique", IEEE Transactions on Biomedical Engineering, Jul. 1992, pp. 752-756, vol. 39, No. 7, IEEE.
V. Jayaraman et al., "OCT Imaging up to 760 kHz Axial Scan Rate Using Single-Mode 1310nm MEMS-Tunable VCSELs with >100nm Tuning Range", OSA/CLEO 2011, 2011.

\* cited by examiner

*Primary Examiner* — Abdullahi Nur (57) ABSTRACT

Disclosed is an optical constant measuring method which includes applying light to a sample including a target material; measuring a first optical signal from light reflected from the sample; grasping a structure of the sample based on the first optical signal; measuring a second optical signal from light penetrating the sample; grasping an overall optical property of the sample based on the second optical signal; and measuring an optical constant of the target material based on the measured structure and optical property of the sample.

9 Claims, 5 Drawing Sheets

OPTICAL CONSTANT MEASURING APPARATUS AND METHOD THEREOF

CROSS-REFERENCE TO RELATED APPLICATIONS

A claim for priority under 35 U.S.C. §119 is made to Korean Patent Application No. 10-2011-0126264 filed Nov. 29, 2011, in the Korean Intellectual Property Office, the entire contents of which are hereby incorporated by reference.

BACKGROUND

The inventive concepts described herein relate to an optical constant measuring apparatus and method thereof.

A measurement technique using light may be used to measure a sample in a noninvasive manner. A method of measuring an optical constant or an electric characteristic of a sample may be used to obtain information associated with a target substance within a sample, for example, a biological material. The optical constant may be a constant indicating an optical property of a sample. The optical constant may include an optical activity of a sample, an angle of rotation on polarized light, and the like.

Information about a path of light incident onto a sample may be required to obtain information associated with a target substance using the optical constant. There may be used a method where a sample is sectioned and a thickness of a section is approximated to an optical path. In this case, however, an error about a sample having a complicated cross-sectional structure may arise. Also, it is impossible to properly measure a sample being not sectioned.

SUMMARY

Example embodiments of the inventive concept provide an optical constant measuring method comprising applying light to a sample including a target material; measuring a first optical signal from light reflected from the sample; grasping a structure of the sample based on the first optical signal; measuring a second optical signal from light penetrating the sample; grasping an optical property of the sample based on the second optical signal; and measuring an optical constant of the target material based on the measured structure and optical property of the sample.

In example embodiments, the light has a broad bandwidth in wavelength.

In example embodiments, the first optical signal includes amplitude and spectrum of light reflected from the sample.

In example embodiments, the second optical signal includes an angle of polarization rotation of light penetrating the sample.

In example embodiments, grasping a structure of the sample based on the first optical signal comprises analyzing a cross sectional structure of the sample using the first optical signal; and calculating a prime optical path of light penetrating the sample based on the analyzed cross sectional structure of the sample.

In example embodiments, calculating a prime optical path of light penetrating the sample comprises extracting a cross sectional boundary plane of the sample using the analyzed cross sectional structure of the sample.

Example embodiments of the inventive concept also provide an optical constant measuring apparatus comprising a first light source generating an incident light; a second light source generating a linearly polarized light; an optical splitter making amplitude distribution on an incident light applied from the first light source into a first split light and a second split light; a reflection mirror reflecting the first split light again to the optical splitter; a dichroic mirror passing the polarized light applied from the second light source and reflecting the second split light applied from the optical splitter; a scanner applying the polarized light transmitting the dichroic mirror and the second split light reflected from the dichroic mirror to a sample; a first optical analysis module measuring an optical signal based on the first split light, reflected from the reflection mirror to be again applied to the optical splitter, and the second split light reflected from the sample to be again applied to the optical splitter; a second optical analysis module measuring an optical signal of the polarized light penetrating the sample; and a result display unit analyzing information from the first and second optical analysis modules to display a result.

In example embodiments, the optical constant measuring apparatus further comprises a first collimator collimating a light incident onto the reflection mirror from the optical splitter; and a second collimator collimating a light incident onto the dichroic mirror from the optical splitter.

In example embodiments, the optical constant measuring apparatus further comprises a polarization controller adjusting a polarization property of a light incident onto the reflection mirror from the optical splitter.

Example embodiments of the inventive concept also provide an optical constant measuring apparatus comprising a light source generating a light; an optical splitter splitting the light from the light source into a first light and a second light through amplitude distribution; a polarization adjusting unit varying a polarization property of a first light applied to the optical splitter; a reflection mirror reflecting the first light applied through the polarization adjusting unit into the optical splitter; a polarizer polarizing a second light applied from the optical splitter; a scanner applying the polarized second light to a sample; a first optical analysis module measuring an optical constant based on the first light, reflected from the reflection mirror to be again applied to the optical splitter, and the second light reflected from the sample to be again applied to the optical splitter; a second optical analysis module measuring an optical signal of the second light penetrating the sample; and a result display unit analyzing information from the first and second optical analysis modules to display a result.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Figure 1:
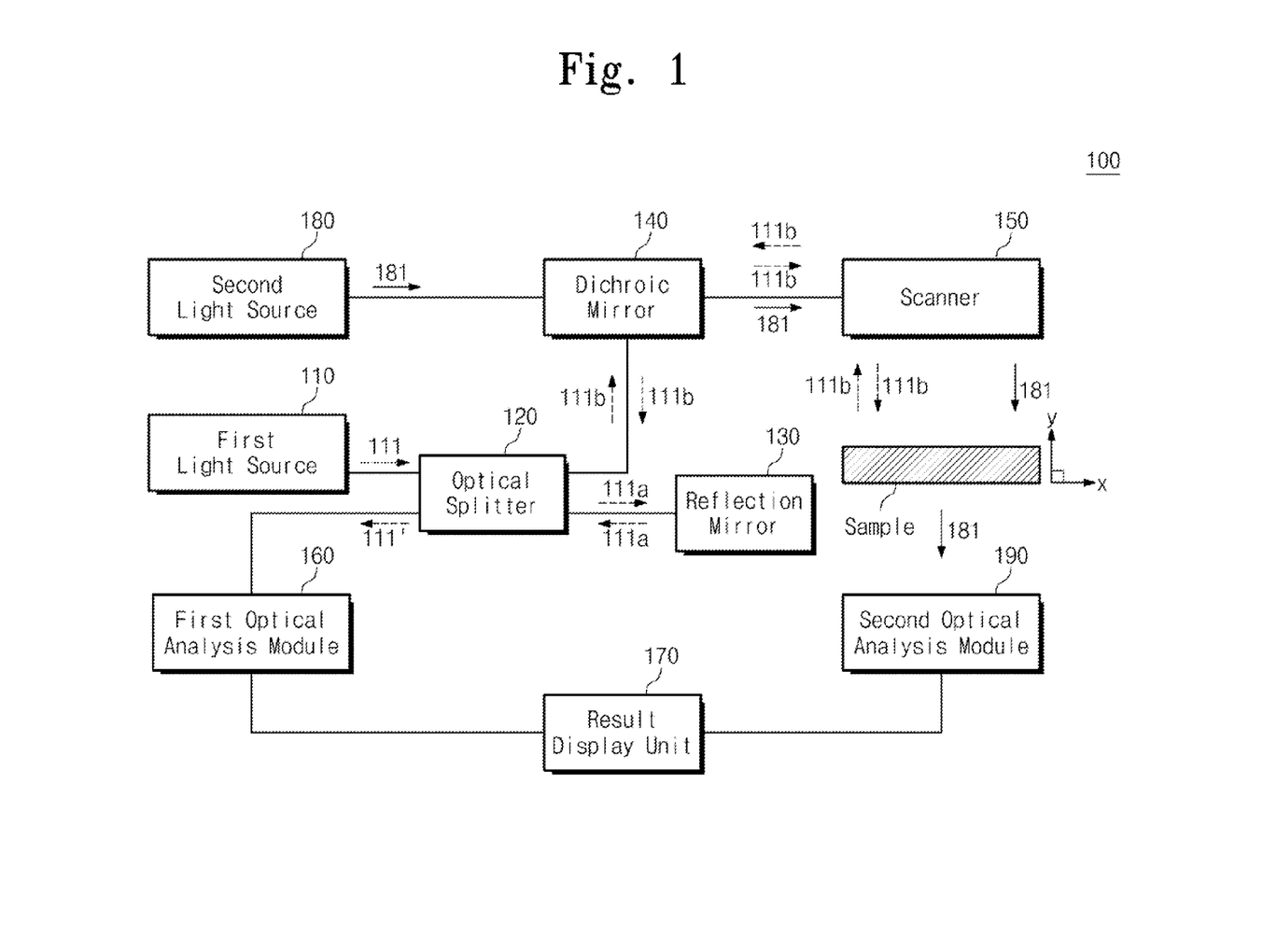
FIG. 1 is a block diagram schematically illustrating an optical constant measuring apparatus according to an embodiment of the inventive concept.

FIG. 1 is a block diagram schematically illustrating an optical constant measuring apparatus according to an embodiment of the inventive concept. Referring to FIG. 1, an optical constant measuring apparatus 100 may have such a structure that an optical coherence tomography unit is coupled with a polarimetry unit.

A first light source 110 may be a broadband light source. The first light source 110 may play a role of a light source of the optical coherence tomography unit. A first light 111 emitted from the first light source 110 may be incident onto an optical splitter 120.

The optical splitter 120 may be configured to amplitude split the first light 111 from the first light source 110. A rate of distribution on the first light 111 may be adjusted at the optical splitter 120. The optical splitter 120 may split the first light 111 into a first split light 111a and a second split light 111b. The first split light 111a may be incident onto a reflection mirror 130, and the second split light 111b may be incident onto a dichroic mirror 140.

The first reflection mirror 130 may reflect the first split light 111a input from the optical splitter 120. A distance between the optical splitter 120 and the reflection mirror 130 may be adjusted. The first split light 111a reflected by the reflection mirror 130 may be incident onto the optical splitter 120.

The dichroic mirror 140 may transmit the second split light 111b input from the optical splitter 120 to a scanner 150. The dichroic mirror 140 may play a role of a reflection mirror with respect to the second split light 111b.

The scanner 150 may apply the second split light 111b input from the dichroic mirror 140 to a sample. A location of the scanner 150 on the sample may be variable. For example, the scanner 150 may apply the second split light 111b to the sample over a parallel movement (e.g., an x-axis direction) with respect to a surface of the sample.

The second split light 111b incident onto the sample from the scanner 150 may be reflected from a predetermined depth of the sample. The second split light 111b may be reflected from various reflection planes in the sample. The reflected second split light 111b may be incident onto the dichroic mirror 140 through the scanner 150. The second split light 111b may be incident onto the optical splitter 120 at the dichroic mirror 140.

Thus, the first split light 111a and the second split light 111b, which are reflected as described above, may interfere at the optical splitter 120 to form a superpositioned light 111'. The superpositioned light 111' may be transmitted to a first optical analysis module 160 from the optical splitter 120.

A strength of the superpositioned light 111' may be changed according to a phase difference between the first split light 111a and the second split light 111b. The phase difference between the first split light 111a and the second split light 111b may be determined according to a difference between optical paths of the first split light 111a and the second split light 111b.

An optical path of the first split light 111a may be adjusted by a distance between the optical splitter 120 and the reflection mirror 130. A distance between the optical splitter 120 and the reflection mirror 130 may be varied as the reflection mirror 130 vibrates with a constant period.

An optical path of the second split light 111b may be determined according to a depth of the sample from which the second split light 111b is reflected. A distance between a first spot from which the first split light 111a is emitted from the optical splitter 120 and a second spot from which the first split light 111a is reflected may be referred to as a first reflection distance. A distance between a first spot from which the second split light 111b is emitted from the optical splitter 120 and a second spot from which the second split light 111b is reflected may be referred to as a second reflection distance. The superpositioned light 111' may indicate an interference signal when a difference between the first reflection distance and the second reflection distance is within a coherence length. The superpositioned light 111' may generate the largest interference signal when an optical path length of the first split light 111a is equal to that of the second split light 111b.

The first optical analysis module 160 may measure an optical signal of the superpositioned light 111' applied from the optical splitter 120. For example, the first optical analysis module 160 may measure variations in amplitude and phase of the superpositioned light 111'. The first optical analysis module 160 may be provided with a location of the reflection mirror 130 when the superpositioned light 111' is input. The first optical analysis module 160 may calculate an optical path of the second split light 111b using the amplitude of the superpositioned light 111' and the location of the reflection mirror 130. This may enable the first optical analysis module 160 to obtain structure information on a y-axis direction of the sample. The first optical analysis module 160 may provide the analysis result to a result display unit 170.

In other example embodiments, the first optical analysis module 160 may measure a variation in amplitude of the superpositioned light 111'. The first optical analysis module 160 may be provided with wavelength information output from the first light source 110 when the superpositioned light 111' is input. The first optical analysis module 160 may obtain structure information on a y-axis direction of the sample, based on the amplitude and spectral information of the input superpositioned light 111'. The first optical analysis module 160 may provide the analysis result to the result display unit 170.

The second light source 180 may be a polarized light source. The second light source 180 may act as a light source of a polarimeter. The second light source 180 may include a polarizer. A second light 181 emitted from the second light source 180 may be incident onto the dichroic mirror 140.

In the dichroic mirror 140, the second light 181 input from the second light source 180 may be passed. That is, the dichroic mirror 140 may pass a wavelength band of the second light 181. The transmitted second light 181 may be incident onto the scanner 150.

The scanner 150 may apply the second light 181 input from the dichroic mirror 140 to the sample. A location of the scanner 150 may be varied with respect to the sample. For example, the scanner 150 may apply the second light 181 to the sample as it shifts in parallel (an x-axis direction) with respect to a surface of the sample.

The second light 181 provided to the sample from the scanner 150 may permeate the sample to be incident onto a second optical analysis module 190. In the second light 181, a polarization plane may be rotated according to an optical activity when it permeates the sample.

The second optical analysis module 190 may measure the second light 181 permeating the sample. For example, the second optical analysis module 190 may measure intensity of the second light 180 and a degree of rotation of a polarization plane. The second optical analysis module 190 may send the measured information to the result display unit 170.

The result display unit 170 may combine information input from the first optical analysis module 160 and information input from the second optical analysis module 190. The result display unit 170 may grasp a structure of the sample based on information input from the first optical analysis module 160. The result display unit 170 may illustrate a cross sectional structure of the sample using the grasped structure.

The result display unit 170 may extract the boundary of the cross sectional structure of the sample by analyzing information provided from the first optical analysis module 160. That is, the result display unit 170 may measure a prime optical path along which light passes with respect to the cross section at which a target material is placed. For example, the result display unit 170 may calculate a prime optical path on a blood vessel of a biological sample. Alternatively, the result display unit 170 may calculate a prime optical path on a flesh portion of a plant sample other than an epidermis portion.

The result display unit 170 may grasp an optical property of the sample based on information input from the second optical analysis module 190. The result display unit 170 may calculate concentration of the target material using the calculated prime optical path and the angle of rotation of the polarization plane input from the second optical analysis module 190. The result display unit 170 may output the calculated information. The result display unit 170 may output the calculated information through a two-dimensional or three-dimensional screen.

The first light source 110 and the second light source 180 may have the strength sufficient to permeate the sample. For example, the first light source 110 and the second light source 180 may be a broadband wavelength swept light source and a He—Ne laser, respectively. Each of the first light source 110 and the second light source 180 can be formed of a broadband wavelength light source using LED. The second light source 180 may output light having a short center wavelength to increase a degree of rotation of a polarization plane. However, since a wavelength of an UV ray domain damages a biological sample, the second light source 180 may use a wavelength of a visible region.

Incident angles of the first split light 111a and the second split light 111b can be corrected to improve the accuracy of the optical constant measuring apparatus according to an embodiment of the inventive concept.

Figure 2:
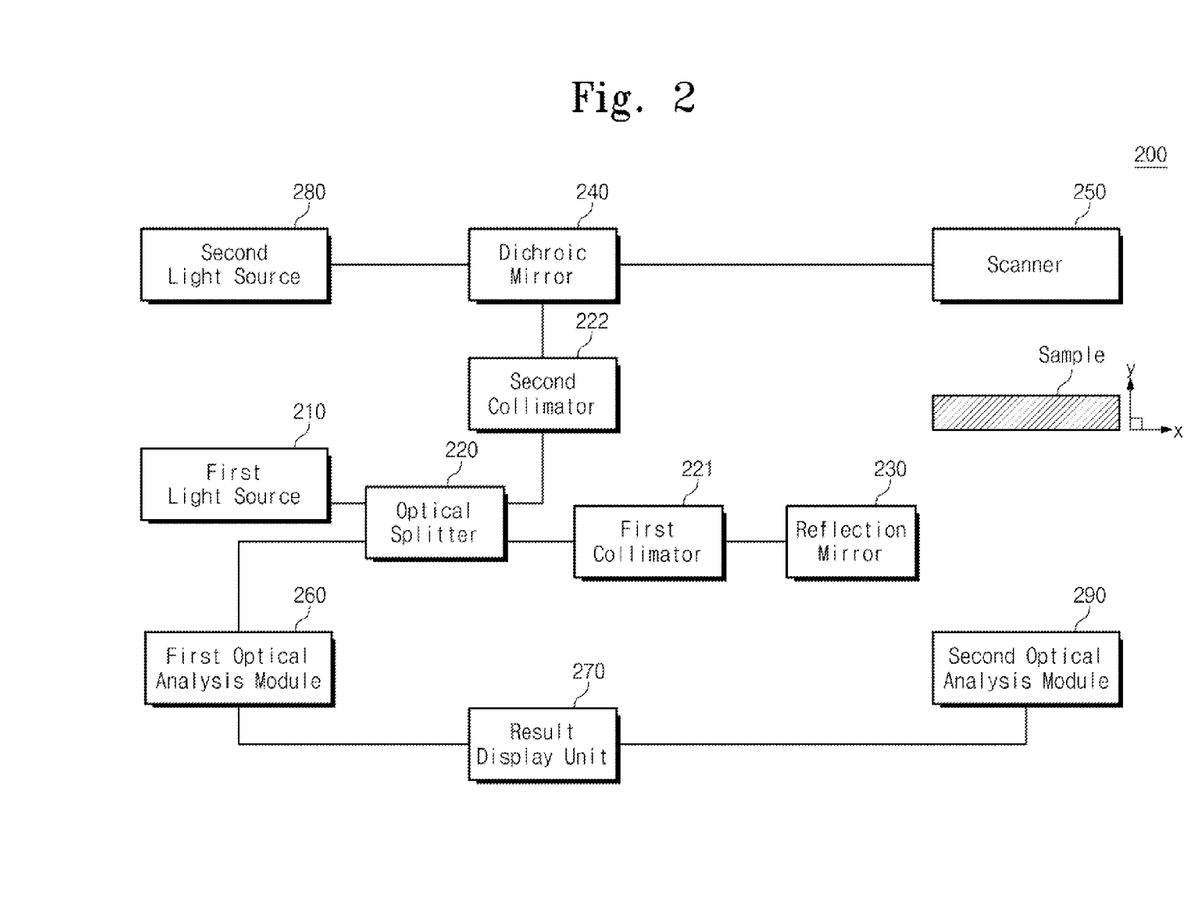
FIG. 2 is a block diagram schematically illustrating an optical constant measuring apparatus according to another embodiment of the inventive concept.

FIG. 2 is a block diagram schematically illustrating an optical constant measuring apparatus according to another embodiment of the inventive concept. Compared with an optical constant measuring apparatus 100 in FIG. 1, an optical constant measuring apparatus 200 in FIG. 2 may further comprise a first collimator 221 and a second collimator 222.

The first collimator 221 may be placed between an optical splitter 220 and a reflection mirror 230. A path of light passing through the first collimator 221 may be corrected. This may be made by the first collimator 221.

When light is transferred to the reflection mirror 230 from the optical splitter 220, a first split light may be transmitted using an optical waveguide. The first split light may be emitted from an end of the optical waveguide. The first split light may be emitted in a radiation shape, and may be incident onto and reflected by a planar reflection mirror 230 in various angles. This may mean that distortion arises when an optical path of the first split light is measured.

The first split light must be incident onto the reflection mirror 230 in parallel to accurately analyze an optical path. The first collimator 221 may collimate light emitted from the end of the optical waveguide. The first collimator 221 may include a lens. Also, the first collimator 221 may include optical parts for optical dispersion compensation.

The second collimator 222 may be placed between the optical splitter 220 and a dichroic mirror 240. A path of light passing through the second collimator 222 may be corrected. This may be made by the second collimator 222. Like the first collimator 221, the second collimator 222 may collimate light emitted in a radiation shape from an end of an optical waveguide which is extended from the optical splitter 220 to the dichroic mirror 240. The second collimator 222 may include a lens.

With the optical constant measuring apparatus of the inventive concept, distortion may be prevented upon measuring of an optical path by correcting an incident angle of light. Thus, a measurement error may be reduced, thus compensating for optical dispersion.

A method for reducing signal loss due to polarization can be used to improve the sensitivity of an optical constant measuring apparatus of the inventive concept.

Figure 3:
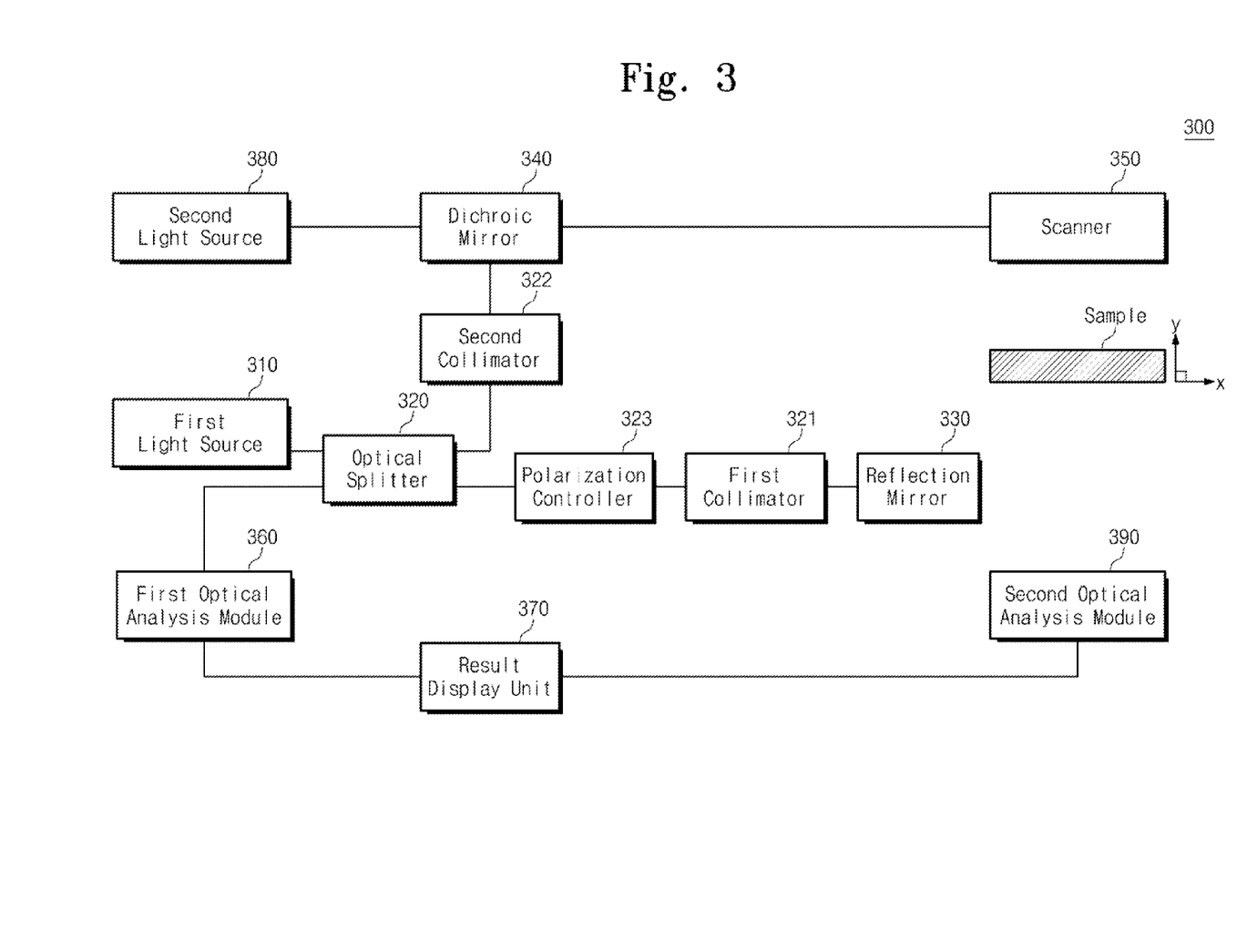
FIG. 3 is a block diagram schematically illustrating an optical constant measuring apparatus according to another embodiment of the inventive concept.

FIG. 3 is a block diagram schematically illustrating an optical constant measuring apparatus according to another embodiment of the inventive concept. Compared with an optical constant measuring apparatus 200 in FIG. 2, an optical constant measuring apparatus 300 in FIG. 3 may further comprise a polarization controller 323.

The polarization controller 323 may be placed between an optical splitter 320 and a first collimator 321. When light is transferred to a reflection mirror 330 from the optical splitter 320, a first split light may be transmitted using an optical waveguide. The first split light may experience a variation in polarization as it passes through the optical waveguide. The first split light experiencing a variation in polarization may be reflected by the reflection mirror 330 to be incident onto the optical splitter 320. In the event that a polarization direction of the first split light is different that a second split light reflected from a sample, an optical signal may become weak when the first split light experiencing a variation in polarization is overlapped with the second split light. Thus, it is difficult to obtain an interference signal of the first split light and the second split light.

The polarization controller 323 may adjust a polarization property of light passing through the optical waveguide. The polarization controller 323 may match polarization of the first split light and the second split light superpositioned at the optical splitter 320. This may enable the polarization controller 323 to maximize a signal of superpositioned light.

With the optical constant measuring apparatus of the inventive concept, a structure analysis error of a sample for measurement of an optical path may be reduced.

In example embodiments, an optical interference cross sectional imaging unit and a polarimetry unit may use different light sources. However, the inventive concept is not limited thereto. For example, one light source can be used instead of first and second light sources.

Figure 4:
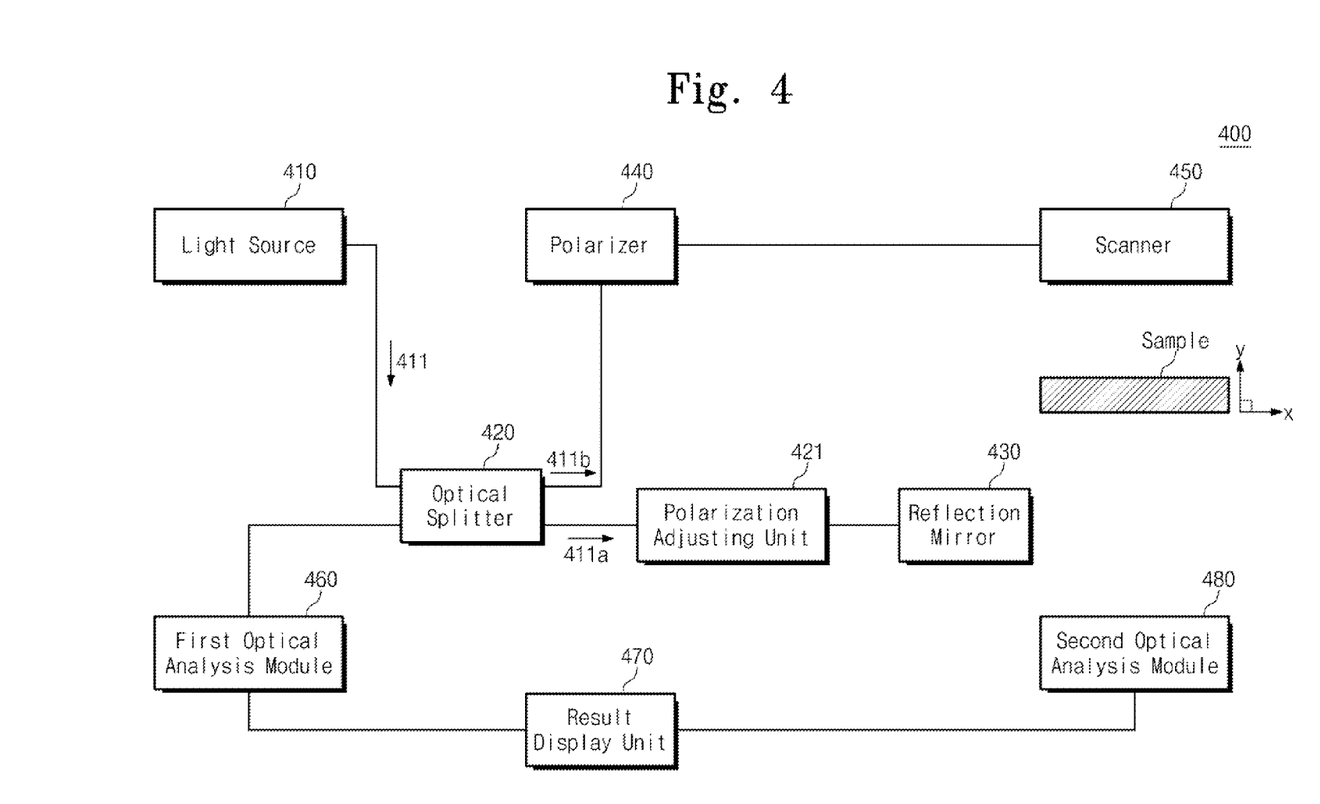
FIG. 4 is a block diagram schematically illustrating an optical constant measuring apparatus according to still another embodiment of the inventive concept.

FIG. 4 is a block diagram schematically illustrating an optical constant measuring apparatus according to still another embodiment of the inventive concept. Referring to FIG. 4, an optical constant measuring apparatus 400 may include a light source 410, an optical splitter 420, a polarization adjusting unit 421, a reflection mirror 430, a polarizer 440, a scanner 450, a first optical analysis module 460, a result display unit 470, and a second optical analysis module 480.

The light source 410 may be a broadband light source or a broadband wavelength swept light source. A first light 411 emitted from the light source 410 may be sent to the optical splitter 420.

The optical splitter 420 may make amplitude distribution on the first light 411 incident from the light source 410. A rate of distribution on the first light 411 may be adjusted at the optical splitter 420. The optical splitter 420 may divide the first light 411 into a first split light 411a and a second split light 411b. The first split light 411a may be incident onto the reflection mirror 430, and the second light 411b may be incident onto the polarizer 440.

The first split light 411a incident onto the reflection mirror 430 may be reflected to be incident onto the optical splitter 420 in a manner similar to that described with reference to FIGS. 1 to 3.

The polarizer 440 may polarize the second split light 411b. The second split light 411b polarized by the polarizer 440 may be sent to the scanner 450. The scanner 450 may apply the second split light 411b to a sample. The polarized second split light 411b applied to the sample may be reflected or permeated.

A reflection component of the polarized second light 411b may be again incident onto the optical splitter 420 through the scanner 450 and the polarizer 440. The polarization adjusting unit 421 may adjust polarization of the first split light 411a to correct a polarization difference between the first split light 411a again incident onto the optical splitter 420 and the second split light. Superpositioned light of the first split light 411a again incident onto the optical splitter 420 and the second split light may be sent to the first optical analysis module 460.

A penetration component of the polarized second light 411b may be incident onto the second optical analysis module 480. The elements 460, 480, and 470 may be substantially the same as those in FIGS. 1 to 3.

With the optical constant measuring apparatus of the inventive concept, an optical interference cross sectional imaging unit and a polarimetry unit may operate using one light source.

Figure 5:
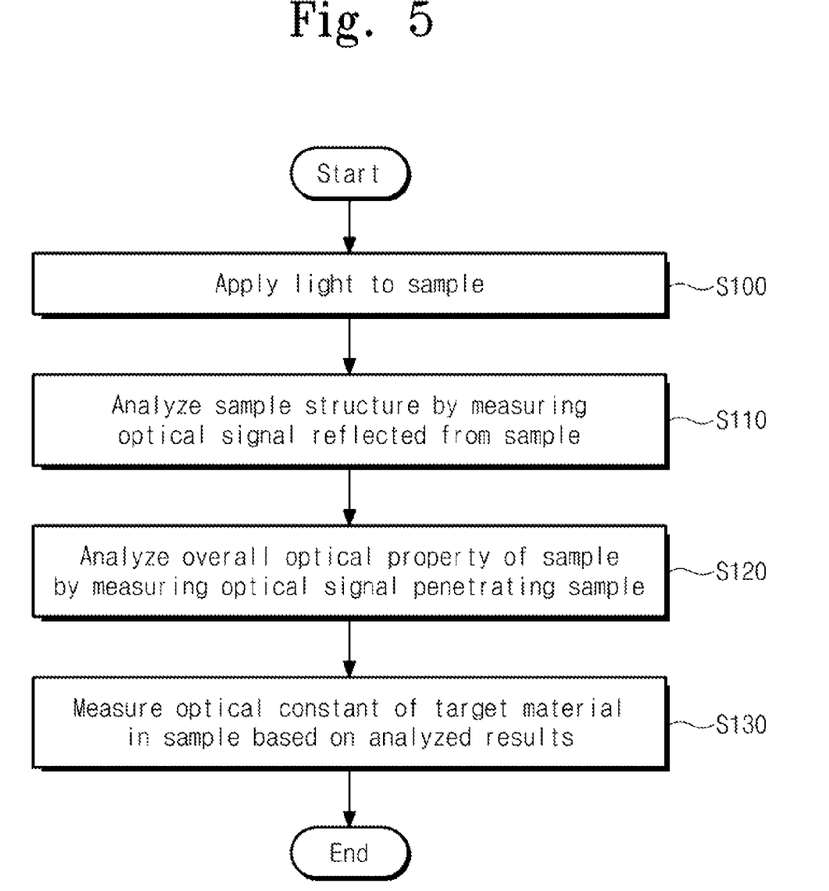
FIG. 5 is a flowchart illustrating an optical constant measuring method according to an embodiment of the inventive concept.

FIG. 5 is a flowchart illustrating an optical constant measuring method according to an embodiment of the inventive concept. Referring to FIG. 5, in operation S100, light may be applied to a sample having a target material to be measured. The light may have a broadband wavelength. The light may be polarized. The light applied to the sample may be reflected or penetrated.

In operation S110, a structure of the sample may be analyzed by measuring an optical signal reflected from the sample. At this time, the optical signal may be optical amplitude, phase, and path. In operation S120, an overall optical property of the sample may be analyzed by measuring an optical signal passing through the sample. At this time, the optical signal may be an angle of rotation of polarized light.

In operation S130, a target material may be measured using the analyzed structure and overall optical property of the sample. At this time, a prime optical path of light penetrating the sample may be calculated using the analyzed structure of the sample. Concentration of the target material may be calculated by combining the calculated prime optical path and the analyzed optical property. The analyzed result may be output visually.

To improve the accuracy of analysis, an incident angle may be adjusted over a transfer of light. Also, polarization may be adjusted over a transfer of light.

With the optical constant measuring method of the inventive concept, an optical constant of a target material may be measured by measuring light reflected from a sample and an optical signal penetrating the sample and combining two information.

While the inventive concept has been described with reference to exemplary embodiments, it will be apparent to those skilled in the art that various changes and modifications may be made without departing from the spirit and scope of the present invention. Therefore, it should be understood that the above embodiments are not limiting, but illustrative.

What is claimed is:

1. An optical constant measuring method comprising:
applying light to a sample including a target material;
measuring a first optical signal from light reflected from the sample;
grasping a structure of the sample based on the first optical signal;
measuring a second optical signal from light penetrating the sample;
grasping an optical property of the sample based on the second optical signal; and
measuring an optical constant of the target material based on the measured structure and optical property of the sample,
wherein grasping a structure of the sample based on the first optical signal comprises:
analyzing a cross sectional structure of the sample using the first optical signal; and
calculating a prime optical path of light penetrating the sample based on the analyzed cross sectional structure of the sample.

2. The optical constant measuring method of claim 1, wherein the light has a broad band-width in wavelength.

3. The optical constant measuring method of claim 1, wherein the first optical signal includes amplitude and spectrum of light reflected from the sample.

4. The optical constant measuring method of claim 1, wherein the second optical signal includes an angle of polarization rotation of light penetrating the sample.

5. The optical constant measuring method of claim 1, wherein calculating a prime optical path of light penetrating the sample comprises extracting a cross sectional boundary plane of the sample using the analyzed cross sectional structure of the sample.

6. An optical constant measuring apparatus comprising:
a first light source generating an incident light;
a second light source generating a linearly polarized light;
an optical splitter making amplitude distribution on an incident light applied from the first light source into a first split light and a second split light;
a reflection mirror reflecting the first split light again to the optical splitter;
a dichroic mirror passing the polarized light applied from the second light source and reflecting the second split light applied from the optical splitter;
a scanner applying the polarized light transmitting the dichroic mirror and the second split light reflected from the dichroic mirror to a sample;
a first optical analysis module measuring an optical signal based on the first split light, reflected from the reflection mirror to be again applied to the optical splitter, and the second split light reflected from the sample to be again applied to the optical splitter;
a second optical analysis module measuring an optical signal of the polarized light penetrating the sample; and
a result display unit analyzing information from the first and second optical analysis modules to display a result.

7. The optical constant measuring apparatus of claim 6, further comprising:
a first collimator collimating a light incident onto the reflection mirror from the optical splitter; and
a second collimator collimating a light incident onto the dichroic mirror from the optical splitter.

8. The optical constant measuring apparatus of claim 6, further comprising:
a polarization controller adjusting a polarization property of a light incident onto the reflection mirror from the optical splitter.

9. An optical constant measuring apparatus comprising:
a light source generating a light;
an optical splitter splitting the light from the light source into a first light and a second light through amplitude distribution;
a polarization adjusting unit varying a polarization property of a first light applied to the optical splitter;
a reflection mirror reflecting the first light applied through the polarization adjusting unit into the optical splitter;
a polarizer polarizing a second light applied from the optical splitter;
a scanner applying the polarized second light to a sample;
a first optical analysis module measuring an optical constant based on the first light, reflected from the reflection mirror to be again applied to the optical splitter, and the second light reflected from the sample to be again applied to the optical splitter;
a second optical analysis module measuring an optical signal of the second light penetrating the sample; and
a result display unit analyzing information from the first and second optical analysis modules to display a result.

* * * * *